(12) United States Patent
Washburn et al.

(10) Patent No.: US 7,973,159 B2
(45) Date of Patent: Jul. 5, 2011

(54) NON-BASIC MELANIN CONCENTRATING HORMONE RECEPTOR-1 ANTAGONISTS

(75) Inventors: William N. Washburn, Titusville, NJ (US); Saleem Ahmad, Wall, NJ (US); Andres S. Hernandez, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/907,451

(22) Filed: Oct. 19, 2010

(65) Prior Publication Data

US 2011/0034375 A1 Feb. 10, 2011

Related U.S. Application Data

(62) Division of application No. 12/109,465, filed on Apr. 25, 2008, now Pat. No. 7,851,622.

(60) Provisional application No. 60/913,901, filed on Apr. 25, 2007.

(51) Int. Cl.
| | |
|---|---|
| C07D 495/04 | (2006.01) |
| A61K 31/5025 | (2006.01) |
| A61K 31/381 | (2006.01) |
| A61P 3/04 | (2006.01) |
| A61P 3/10 | (2006.01) |
| A61P 25/22 | (2006.01) |
| A61P 25/24 | (2006.01) |

(52) U.S. Cl. ...................................... 544/235; 514/248
(58) Field of Classification Search .................. 544/235; 514/248
See application file for complete search history.

(56) References Cited

U.S. PATENT DOCUMENTS

| | | |
|---|---|---|
| 2007/0093509 A1 | 4/2007 | Washburn et al. |
| 2009/0298794 A1 | 12/2009 | Washburn et al. |

FOREIGN PATENT DOCUMENTS

| | | |
|---|---|---|
| WO | WO 03/033476 | 4/2003 |
| WO | WO 2005/042541 | 5/2005 |
| WO | WO 2005/103039 | 11/2005 |
| WO | WO 2007/011284 | 1/2007 |
| WO | WO 2007/011286 | 1/2007 |

OTHER PUBLICATIONS

Banker, G.S. et al., eds., Modern Pharmaceutics, Third Edition, pp. 451 and 596, Marcel Dekker, Inc., publ. (1996).
Vippagunta, S.R. et al., "Crystalline solids", Advanced Drug Delivery Reviews, vol. 48, pp. 3-26 (2001).
West, A.R., Solid State Chemistry and its Applications, pp. 358 and 365, John Wiley & Sons, publ. (1988).
Wolff, M.E., ed., Burger's Medicinal Chemistry and Drug Discovery, Fifth Edition, vol. 1: Principles and Practice, pp. 975-977, John Wiley & Sons, Inc., publ. (1995).

*Primary Examiner* — Venkataraman Balasubramanian
(74) *Attorney, Agent, or Firm* — Burton Rodney; Jing G. Sun

(57) ABSTRACT

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

where $R^1$, $R^{1a}$, $R^{1b}$, A, $R^3$, $R^4$, $R^5$, $R^{5b}$ and $R^6$ are as defined herein.

20 Claims, No Drawings

NON-BASIC MELANIN CONCENTRATING HORMONE RECEPTOR-1 ANTAGONISTS

This application is a divisional of U.S. application Ser. No. 12/109,465, filed Apr. 25, 2008, now U.S. Pat. No. 7,851,622, which claims priority benefit of U.S. Provisional Application Ser. No. 60/913,901, filed Apr. 25, 2007.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J. Pharmacol*, 438:129-135 (2002), *Nat. Med.*, 8:825-830 (2002), *Eur. J. Pharmacol.*, 497:41-47 (2004).

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (Kowalski, T. J. et al., *Expert Opin. Invest. Drugs,* 13:1113-1122 (2004)). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (Ulven, T., *J. Med. Chem.,* 48:5684-5697 (2005)). However, incorporation of this basic amine in a MCHR1 antagonist increases substantially the probability of binding to off-target ion-channels and biogenic amine receptors.

Herein we describe a series of novel high affinity selective MCHR1 antagonists that were obtained by replacement of the basic amine moiety described in WO 03/033476 with non-basic polar functionalities. Moreover, this structural modification results in unexpected ablation of binding to other biogenic amine receptors as well as binding to the HERG receptor in the heart. The reduction/abolition of affinity for the HERG receptor is especially important since ligand occupancy is associated with initiation of fatal arrhythmias.

SUMMARY OF THE INVENTION

The present invention is directed to compounds having the following Formula I, methods for using them for the treatment of obesity, and pharmaceutical compositions comprising compounds of Formula I. The compounds of the present invention are described as follows:

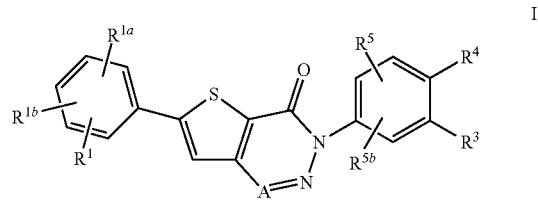

including pharmaceutically acceptable salts, solvates, and prodrugs thereof,
wherein,
A is N or $CR^2$;
$R^1$, $R^{1b}$ and $R^{1a}$ are the same or different and are each independently selected from H, halo, lower alkyl, cycloalkyl, $CF_3$, alkoxy or thioalkoxy;
$R^2$ is H or lower alkyl;
$R^3$ is H, halo, lower alkyl, cycloalkyl, $CF_3$, lower alkoxy, thioalkoxy, or CN;
$R^4$ is —OH or -G-D-$Z_n$;
$R^5$ and $R^{5b}$ are the same or different and are each independently selected from H, halo, and lower alkyl;
n is 1 to 3;
G is O or S;
D is selected from the group consisting of a direct bond, lower alkyl, cycloalkylalkyl, cycloalkyl and

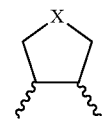

wherein X is —O—, —S—, —SO— or —$SO_2$—;
Z is hydrogen, hydroxyl, polyhaloalkyl, lower alkyl, lower alkoxy, cycloalkyl, cycloalkoxy, $OCONR^6R^7$, CN, $CONR^8R^9$, $SOR^{10}$, $SO_2R^{11}$, $NR^{12}COR^{13}$, $NR^{14}CO_2R^{15}$, $COR^{16}$, a 5- to 6-membered heteroaryl, or a 4- to 6-membered heterocycloalkyl containing no more that two heteroatoms wherein the heteroatoms are independently —O—, —S—, —SO— or —$SO_2$—;
$R^6$, $R^7$, $R^8$, $R^9$, $R^{12}$ and $R^{14}$ are the same or different and are each independently selected from H, lower alkyl or cycloalkyl or $R^6$ and $R^7$ and/or $R^8$ and $R^9$ together with the atoms to which they are attached may form a 4- to 7-membered ring; and
$R^{10}$, $R^{11}R^{13}$, $R^{15}$ and $R^{16}$ are the same or different and are each independently selected from lower alkyl or cycloalkyl.

In some embodiments of the present invention, $R^4$ is -G-D-$Z_n$ and D is lower alkyl.

In some embodiments of the present invention, Z is $COR^{16}$, —OH, dioxylanyl, or $CF_3$.

In some embodiments of the present invention, $R^3$ is methoxy.

In some embodiments of the present invention $R^1$ is Cl.

In some embodiments of the present invention, $R^{1a}$, $R^{1b}$, $R^5$, and $R^{5b}$ are H.

In some embodiments of the present invention, $R^4$ is -G-D-$Z_n$; D is lower alkyl; Z is —OH, dioxylanyl, or $CF_3$; $R^3$ is methoxy; $R^1$ is Cl; and $R^{1a}$, $R^{1b}$, $R^5$, and $R^{5b}$ are H.

In some embodiments of the present invention, pharmaceutical compositions are provided comprising at least one compound having the Formula I, as described above, and at least one pharmaceutically acceptable diluent or carrier.

In some embodiments of the present invention, methods are provided for treating a patient suffering from an MCHR-1 modulated disease or disorder such as, for example, obesity, diabetes, depression or anxiety by administration of a therapeutically effective dose of a compound according to Formula I, optionally in combination with other therapeutic agents, such as those described below.

DEFINITIONS

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" or "lower cycloalkyl" as employed herein alone or as part of another group includes saturated or partially unsaturated (containing 1 or 2 double bonds) cyclic hydrocarbon groups containing 1 to 3 rings, any one of which may optionally be a Spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

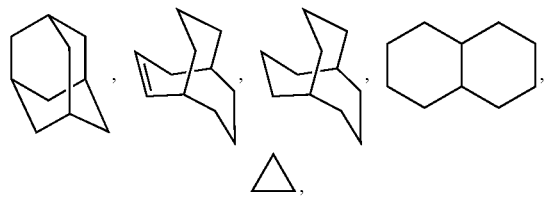

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

Unless otherwise indicated, the term "cycloalkoxy" or "lower cycloalkoxy" as employed herein alone or as part of another group, represents a 4-, 5- or 6-membered saturated ring containing an oxygen in the ring and includes

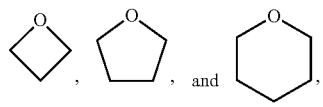

and which may be optionally substituted with 1 or 2 of any of the substituents as set out for cycloalkyl.

The term "heterocycloalkyl" as used herein, alone or as part of another group, represents an unsubstituted or substituted stable 4- to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyrazinyl, pyrimidinyl, pyridazinyl, oxazolyl, oxazolidinyl, isooxazolyl, isoxazolidinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature 1982-1995*, Elsevier Science, Inc., Tarrytown, N.Y. (1996); and references therein. The heterocycloalkyl may optionally be substituted with at least one of F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

The term "aryl" herein alone or as part of another group refers to monocyclic or bicyclic aromatic rings, e.g., phenyl, substituted phenyl and the like, as well as groups which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 1982-1995, Elsevier Science, Inc., Tarrytown, N.Y. (1996); and references therein. Further, "heteroaryl", as defined herein, may optionally be substituted with one or more substituents such as the substituents included above in the definition of "substituted alkyl" and "substituted aryl". Examples of heteroaryl groups include the following:

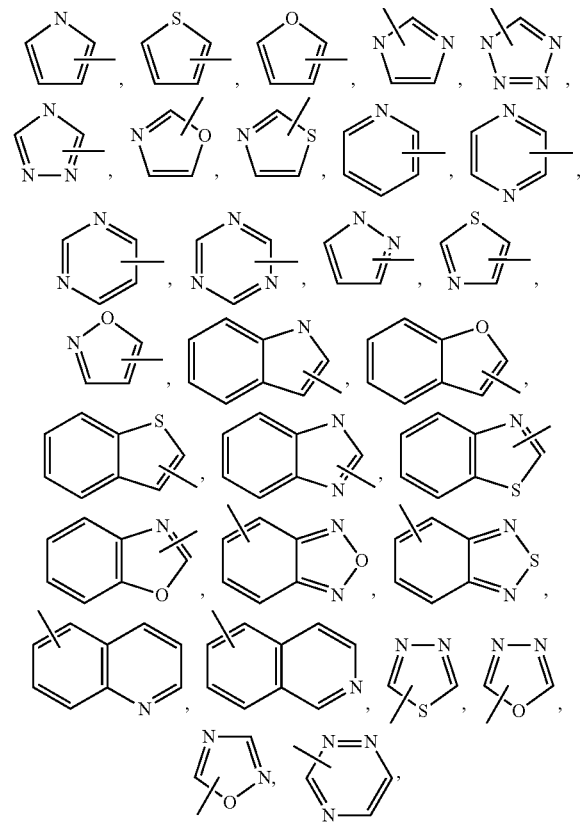

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug" encompasses both the term "prodrug esters" and the term "prodrug ethers". The term "prodrug esters" as employed herein includes esters and carbonates formed by reacting one or more hydroxyls of compounds of formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

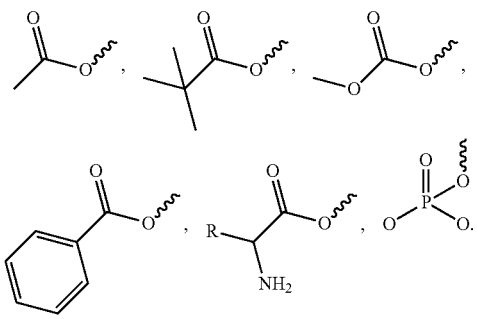

The term "prodrug ethers" include both phosphate acetals and O-glucosides. Representative examples of such prodrug ethers include

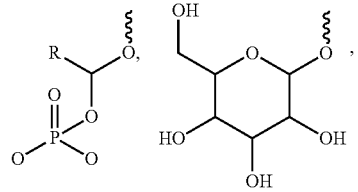

DETAILED DESCRIPTION

The present invention is directed to compounds having the following Formula I, including pharmaceutically acceptable salts, solvates, and prodrugs thereof:

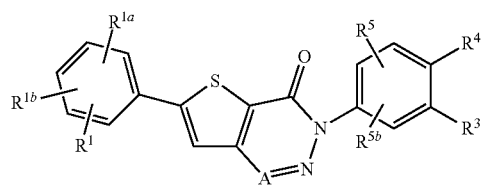

wherein,

A is N or CR$^2$;

R$^1$, R$^{1b}$ and R$^{1a}$ are the same or different and are each independently selected from H, halo, lower alkyl, cycloalkyl, CF$_3$, alkoxy or thioalkoxy;

$R^2$ is H or lower alkyl;
$R^3$ is H, halo, lower alkyl, cycloalkyl, $CF_3$, lower alkoxy, thioalkoxy, or CN;
$R^4$ is —OH or -G-D-$Z_n$;
$R^5$ and $R^{5b}$ are the same or different and are each independently selected from H, halo or lower alkyl;
n is 1 to 3;
G is O or S;
D is selected from the group consisting of a direct bond, lower alkyl, cycloalkylalkyl, cycloalkyl and

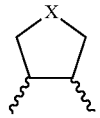

wherein X is —O—, —S—, —SO— or —SO$_2$—, for example, 1,3-dioxalane, 1,3-dithiolane, tetrahydrofuran, tetrahydrothiophene, tetrahydrothiophene-1-oxide, sulfolane, 1,4-oxathiane, 1,4-oxathiane-1-oxide, 1,4-oxathiane-1,1-dioxide, 1,3-dithiane, 1,4-dithiane, 1,3-dioxane, 1,4-dioxane, 1,3-oxathiolane, 1,3-oxathiolane-1-oxide, 1,3-oxathiolane-1,1-dioxide;

Z is hydrogen, hydroxyl, polyhaloalkyl, lower alkyl, lower alkoxy, cycloalkyl, cycloalkoxy, OCONR$^6$R$^7$, CN, CONR$^8$R$^9$, SOR$^{10}$, SO$_2$R$^{11}$, NR$^{12}$COR$^{13}$, NR$^{14}$CO$_2$R$^{15}$, COR$^{16}$, a 5- to 6-membered heteroaryl, or a 4- to 6-membered heterocycloalkyl containing no more that two heteroatoms wherein the heteroatoms are independently —O—, —S—, —SO— or —SO$_2$—;

R$^6$, R$^7$, R$^8$, R$^9$, R$^{12}$ and R$^{14}$, are the same or different and are each independently selected from H, lower alkyl or cycloalkyl or R$^6$ and R$^7$ and/or R$^8$ and R$^9$ together with the atoms to which they are attached may form a 4- to 7-membered ring; and R$^{10}$, R$^{11}$ R$^{13}$, R$^{15}$ and R$^{16}$ are the same or different and are each independently selected from lower alkyl or cycloalkyl.

According to some embodiments of the present invention, pharmaceutical compositions are provided, comprising at least one compound having Formula I, as described herein, and at least one pharmaceutically acceptable diluent or carrier. The pharmaceutical compositions of the present invention, may optionally include at least one additional therapeutic agent selected from the group consisting of anti-obesity agents; anti-diabetic agents, appetite suppressants; cholesterol/lipid-lowering agents, and HDL-raising agents, as defined herein.

The present invention is also directed to pharmaceutical combinations, comprising at least one compound having the Formula I, and at least one additional therapeutic agent, selected from the group consisting of anti-obesity agents; anti-diabetic agents, appetite suppressants; cholesterol/lipid-lowering agents, and HDL-raising agents, as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PTP-1B inhibitors.

According to one embodiment of the present invention, the additional therapeutic agent is an antiobesity agent selected from group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, Pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor antagonists.

According to one embodiment of the present invention, methods are provided for treating obesity in a patient in need of such treatment, comprising administering a therapeutically effective amount of at least one compound according to Formula I alone or in combination with one or more additional antiobesity agents, wherein the obesity agent is selected from those described herein.

According to one embodiment of the present invention, methods are provided for treating diabetes, especially Type II diabetes, in a patient in need of such treatment, comprising administering a therapeutically effective amount of at least one compound according to Formula I alone or in combination with one or more additional antidiabetic agents, wherein the diabetic agent is described herein.

According to one embodiment of the present invention, methods for treating depression in a patient are provided, comprising administering a therapeutically effective amount of at least one compound according to Formula I.

According to one embodiment of the present invention, methods are provided for treating anxiety in a patient in need of such treatment, comprising administering a therapeutically effective amount of a compound having Formula I.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tent-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the present application can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (arnantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having difficult modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the application.

Examples of suitable anti-obesity agents for use in combination with the compounds of the present application include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor antagonists, such as SR-141716 (Sanofi) or SLV-319 (Solvay) and DGAT inhibitors such as those described in WO 2006/134317 (A1) (Astra Zeneca), WO 2006/044775 (A2) (Bayer), WO 2006/06019020 (A1) (Sankyo), WO 2006/082010 (A1) (Roche), WO 2004/047755 (A2) (Japan Tobacco, Tularik), and WO 2005/0727401 (A2) (Amgen, Japan Tobacco).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors including dapagliflozin and sergliflozin, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present application may be employed with a PPAR α/γ dual agonist such as MK-767/KRP-297 (Merck/Kyorin; as described in, Yajima, K. et al., *Am. J. Physiol. Endocrinol. Metab.,* 284:E966-E971 (2003)), AZ-242 (tesaglitazar; Astra-Zeneca; as described in Ljung, 13. et al., *J. Lipid Res.,* 43:1855-1863 (2002)); muraglitazar; or the compounds described in U.S. Pat. No. 6,414,002.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.,* 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design,* 2:1-40 (1996).

In addition, other squalene synthetase inhibitors suitable for use herein include the terpenoid pyrophosphates disclosed by Ortiz de Montellano, P. et al., *J. Med. Chem.,* 20:243-249 (1977), the farnesyl diphosphate analog A and presqualene pyrophosphate (PSQ-PP) analogs as disclosed by Corey et al., *J. Am. Chem. Soc.,* 98:1291-1293 (1976), phosphinylphosphonates reported by McClard, R. W. et al., *J. Am. Chem. Soc.,* 109:5544 (1987) and cyclopropanes reported by Capson, T. L., Ph.D., dissertation, Dept. Med. Chem., Univ. Utah, Abstract, Table of Contents, pp. 16, 17, 40-43, 48-51, Summary (June 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-SEPHADEX® (Secholex, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in *Drugs of the Future,* 24:9-15 (1999), (Avasimibe); Nicolosi et al., "The ACAT inhibitor, Cl-1011 is effective in the prevention and regression of aortic fatty streak area in hamsters", *Atherosclerosis* (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause et al., "ACAT inhibitors: physiologic mechanisms for hypolipidemic and anti-atherosclerotic activities in experimental animals", *Inflammation: Mediators Pathways,* pp. 173-198, Ruffolo, R. R., Jr.; et al., eds., CRC, Boca Raton, Fla., publ., (1995); Sliskovic et al., "ACAT inhibitors: potential anti-atherosclerotic agents", *Curr. Med. Chem.,* 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", *Chemtracts: Org. Chem.,* 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis,* 115:45-63 (1995) and *J. Med. Chem.,* 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in *Drugs of the*

Future, 24:425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equal, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-1 (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

Compounds of formula I where A is N may be prepared by the reaction sequence outlined in Scheme 1. Depending on the particular molecule of formula I being prepared, $R^4$ can either be fully completed prior to or elaborated after assemblage of the core structure of formula I. Compound 1, which are commercially available or readily prepared by one skilled in the arts, upon sequential treatment with $POCl_3$ followed by hydroxylamine can be converted to compound 2. Compound 3 can be prepared by heating compound 2 with methyl mercaptoacetate in a solvent such as methanol containing a base such as sodium methoxide. Compound 4 can be prepared by hydrolysis of compound 3 with base such as LiOH, NaOH or KOH in a solvent such as aq MeOH or EtOH optionally containing THF. Compound 8 can be prepared by condensation of compound 4 with compound 7 employing standard amide coupling reagents such as HATU (O-(7-azabenzotriazol-1-yl)-N,N,N',N'-tetramethyluronium $PF_6$), PyBroP, EDC, or DCC in a solvent such as DMF, $CH_2Cl_2$, THF in the presence of a base such as $Et_3N$ or $EtN(iPr)_2$.

Compound 7 is available from commercial nitrophenols or nitrothiophenols following masking of the phenolic OH or SH functionality with a protecting group (P-group) to generate compound 6 followed by reduction of the nitro moiety to $NH_2$. The P-group can either be $R^4$ of compounds of Formula I or be a transient group that will be removed and replaced with $R^4$ at a later stage in the sequence by employing transformations known to one skilled in the arts. P-groups can be introduced by heating compound 5 at temperatures ranging from 20-170° C. with an alkylating agent such as alkyl halides, tosylates or mesylates or epoxides or with acylating agents such anhydrides in the presence of a weak base such as sodium bicarbonate, sodium dibasic phosphate, potassium carbonate in a solvent such as DMF, THF, MeCN or aqueous mixtures thereof from 1 to 24 hr. Reduction of compound 6 to generate compound 7 can be achieved by Pd catalyzed hydrogenation under $H_2$ atmosphere in a solvent such as ethanol or ethyl acetate or by metal promoted reductions such as iron/HCl or stannous chloride.

Compounds of formula I can be directly prepared by treatment of compound 8 with $NaNO_2$ and HOAc as described in WO 2007/011286 if the P-group corresponds to $R^4$. Alternatively compound 9 is obtained following treatment of compound 8 with $NaNO_2$ and HOAc. Compound 9 requires removal of the P-group (for example $BBr_3$ in $CH_2Cl_2$ when the P-group is methyl) to generate phenols or thiophenols 10. Subsequent alkylation of 10 with an "activated $D-Z_n$" component in the presence of a base such as potassium carbonate in a solvent such as DMF, THF, MeCN or aqueous mixtures thereof at temperatures of 50-150° C. for 1-24 hr will generate compounds of formula I. The "activated $D-Z_n$" can be an epoxide or a $Z_n$-D-covalently linked to a leaving group, either of which are commercially available or readily prepared by one skilled in the art.

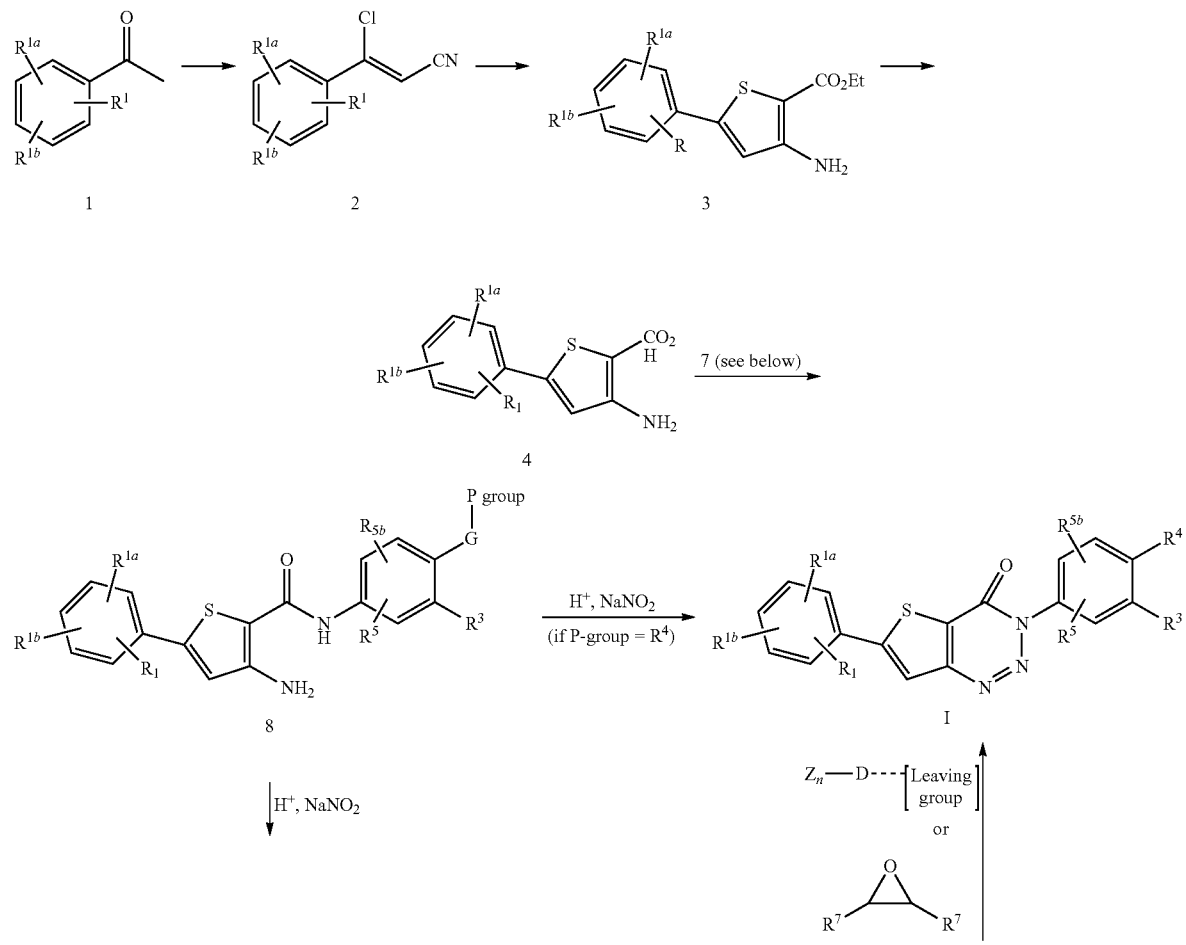

Scheme 1

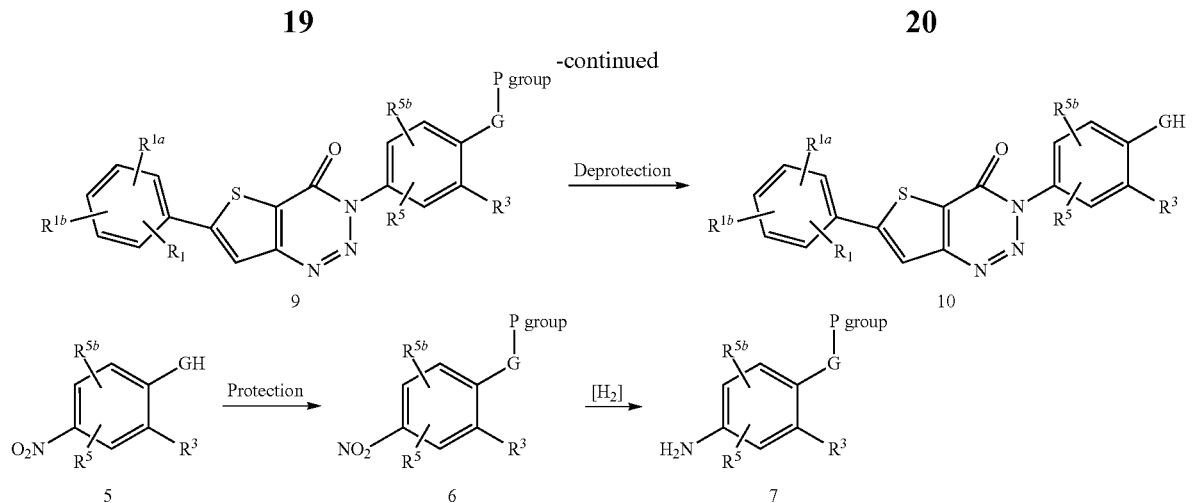

Scheme 2 illustrates an alternative means of preparation of compounds of formula I where A is N. Compound 11 is readily prepared from condensation of benzyl amine with compound 4 under conditions employing standard amide forming conditions known to one skilled in the art. Compound 12 can be prepared by treatment of compound 11 with $NaNO_2$ and HOAc as described in WO 2007/011286. Compound 13 may be prepared from compound 12 upon debenzylation employing $Pd/H_2$ in a solvent such as mixtures of ethanol and ethyl acetate. Compounds of formula I can be prepared following cupric oxide catalyzed arylation 13 with compound 14 in a solvent such as dioxane in the presence of a base such as tribasic potassium phosphate by heating at temperatures of 100-160° C. for up to 36 hr followed by subsequent, if needed, conversion of the P-group to $R^4$.

Compound 14 where X is a borate are commercially available or can be obtained by n-BuLi mediated lithium halogen exchange of the corresponding halide 14 followed by trapping with methyl borate. Compound 14 where X is a halogen are obtained from compound 15 following protection of the phenol or thiophenol moiety. Compound 15 is either commercially available or readily prepared by standard transformations from commercial aromatic compounds by electrophilic aromatic substitution reactions. As appropriate, P-group 15 may be $R^4$ or a protected component thereof such as the corresponding methyl ether which after deprotection is subsequently elaborated to the desired $R^4$ appendage as outlined in Scheme I.

Scheme 2

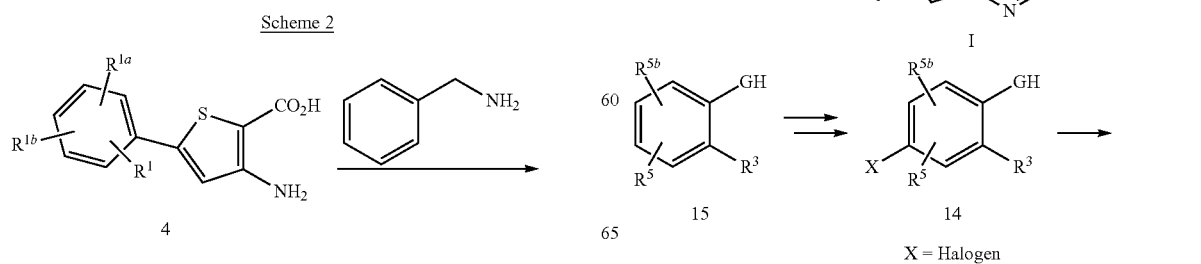

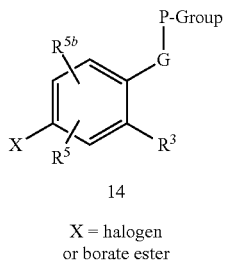

14

X = halogen
or borate ester

Scheme 3 outlines a general synthetic route for compounds of formula I where A is $CR^2$. Compound 18 can be prepared by Pd catalyzed coupling of compound 17 with the commercially available compound 16. Compound 17 is commercially available or readily prepared by one skilled in the art. Compound 19 can be prepared from compound 18 by sequential n-butyl lithium mediated metalation in a solvent such as THF and subsequent addition to an appropriate N,N-dimethyl alkylcarboxamide or DMF in a solvent such as THF followed by aqueous acid hydrolysis. Subsequently compound 20 can be generated by condensation of compound 19 with hydrazine upon heating at reflux for 1 to 4 days in a solvent such as methanol or ethanol. Copper oxide promoted coupling of compound 20 with compound 14, where X is halogen, in a solvent such as dioxane in the presence of a base such as tribasic potassium phosphate by heating at temperatures of 100-160° C. for up to 36 hr yields compounds of formula I directly if P-group is $R^4$. Otherwise, compounds of formula I are obtained following deprotection of the cupric oxide product 21 and subsequent alkylation of the free phenol or thiophenol 22 as previously described in Scheme 1.

Scheme 3

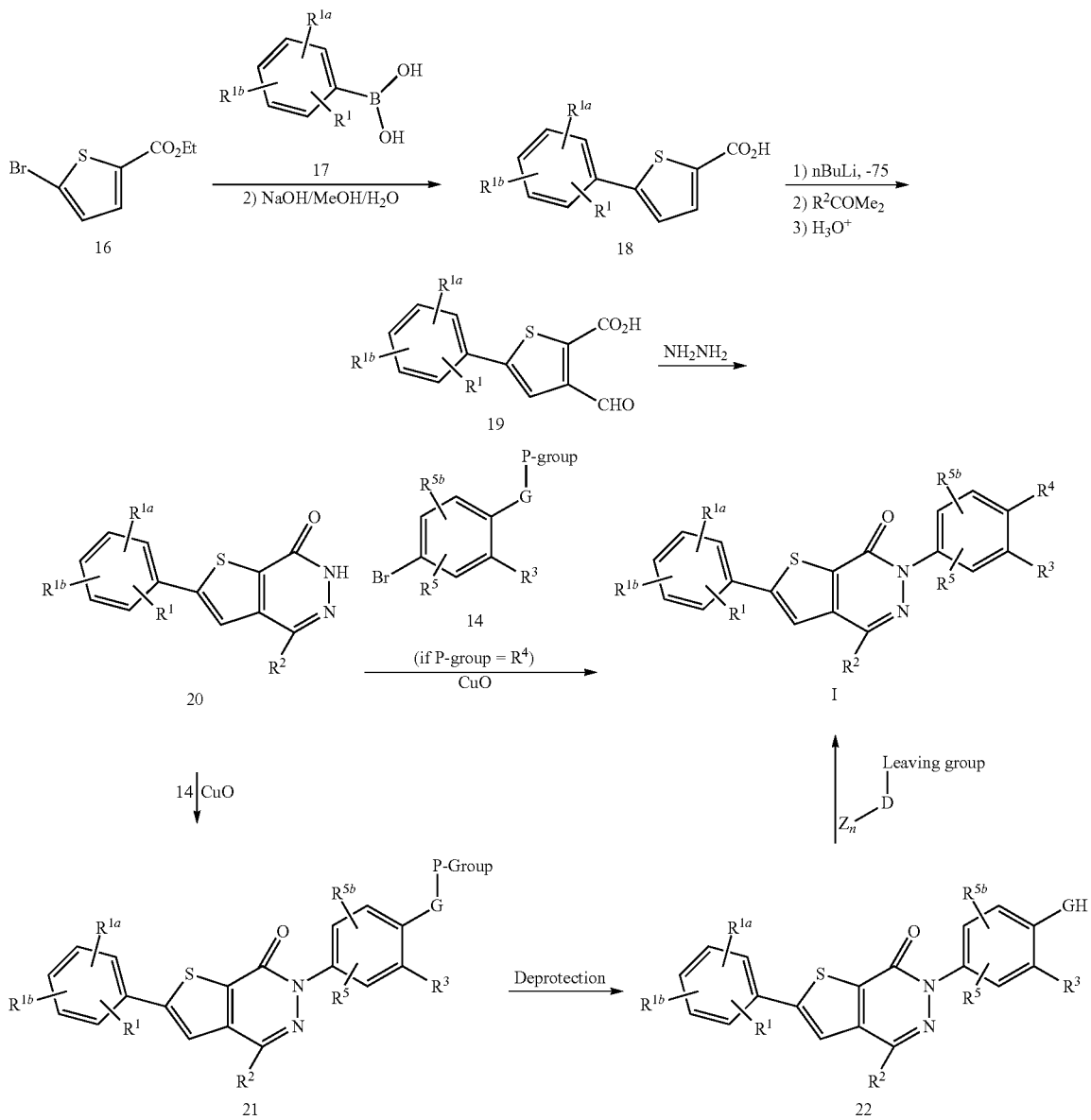

ABBREVIATIONS

The following abbreviations are employed herein:

Ph=phenyl
Bn=benzyl
t-Bu=tertiary butyl
Me=methyl
Et=ethyl
TMS=trimethylsilyl
TBS tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3N$=triethylamine
DMAP=4-dimethylaminopyridine
$NaBH_4$=sodium borohydride
n-BuLi=n-butyllithium
Pd/C=palladium on carbon.
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The following Examples 1 to 9 serve to better illustrate, but not limit, some of the preferred embodiments of the application.

Example 1

6-(4-Chlorophenyl)-3-(4-(2-hydroxy-2-methylpropoxy)-3-methoxyphenyl)-thieno[3,2-d][1,2,3]triazin-4(3H)-one

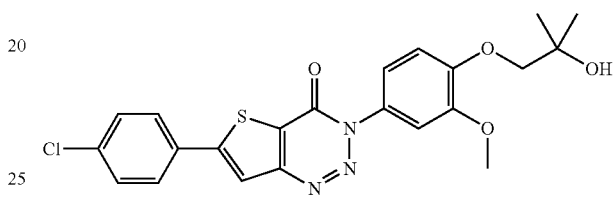

A.
3-Amino-5-(4-chlorophenyl)thiophene-2-carboxylic acid

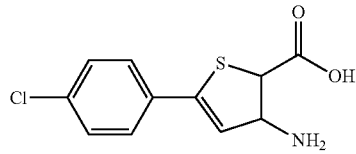

The title compound was prepared according to the procedure described in patent application WO 2007/011286.

B.
1-(4-Amino-2-methoxyphenoxy)-2-methylpropan-2-ol

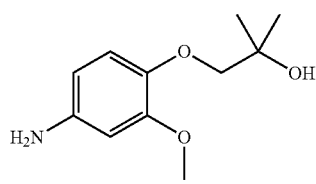

The title compound was prepared following the procedure described in U.S. Provisional Application No. 60/730,453.

C. 3-Amino-5-(4-chlorophenyl)-N-(4-(2-hydroxy-2-methylpropoxy)-3-methoxyphenyl)thiophene-2-carboxamide

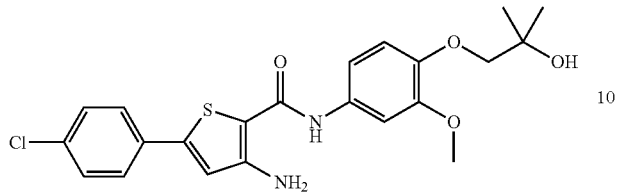

Following addition of O-(7-azabenzotriazol-1-yl)-N,N,N',N'-tetramethyluronium hexafluorophosphate (HATU) (571 mg, 1.50 mmol) and N,N-diisopropylethyl-amine (0.64 mL, 3.67 mmol) to a solution of the amide described in Part A of Example 1 (298 mg, 1.17 mmol) in NMP (6.0 mL) were added, the resulting solution was stirred at RT for 2 h. A solution of the aniline described in Part B (257 mg, 1.22 mmol) in $CH_2Cl_2$ (2.0 mL) was then added; whereupon, the stirred mixture was heated at 80° C. for 4.5 h. After cooling to RT, water (75 mL) was added followed by sat'd $NaHCO_3$ (15 mL) prior to extraction of the aqueous mixture (pH ~9) with EtOAc (3×50 mL). The combined organic extracts were washed with water (50 mL), dried ($Na_2SO_4$) and concentrated under vacuum. Chromatography ($SiO_2$ 230-400 mesh, 1:4 $CH_2Cl_2$/EtOAc) of the crude product yielded the desired amide (332 mg, 63.2% yield) as a yellow solid: MS (electrospray, + ions) m/z 447 (M+H).

D. 6-(4-Chlorophenyl)-3-(4-(2-hydroxy-2-methylpropoxy)-3-methoxyphenyl)-thieno[3,2-d][1,2,3]triazin-4(3H)-one

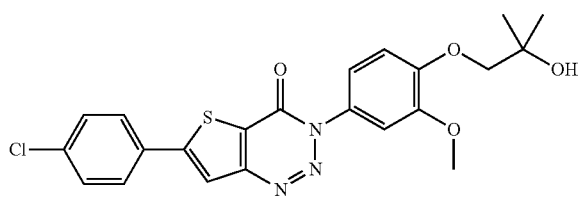

To a solution of the anilide described in Part C (272 mg, 0.61 mmol) in AcOH (7.4 mL) and water (1.50 mL) was added $NaNO_2$ (44.0 mg, 0.64 mmol). The mixture was stirred at RT for 1.2 h before being poured into water (50 mL). After adjusting the pH to 9 by addition of 1M NaOH, the suspension was allowed to stand at RT overnight. The resulting precipitate was collected by filtration, washed with water and dried to afford the title compound (264 mg, 95% yield) as a brownish solid: MS (electrospray, + ions) m/z 458 (M+H). $^1$H NMR δ ($CD_2Cl_2$) 7.84 (s, 1H), 7.69 (d, J=8.8 Hz, 2H), 7.47 (d, J=8.8, 2H), 7.13 (m, 2H), 7.02 (d, J=8.8 Hz, 1H), 3.86 (s, 2H, overlapped), 3.85 (s, 3H, overlapped), 1.31 (s, 6H).

Example 2

6-(4-Chlorophenyl)-3-(3-methoxy-4-(2-oxopropoxy)phenyl)thieno[3,2-d][1,2,3]triazin-4(3H)-one

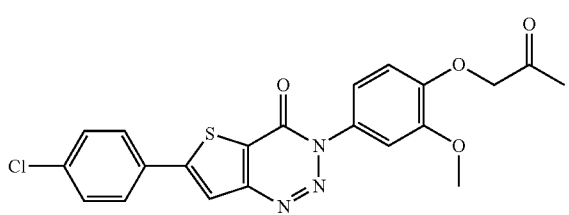

A. 2-Methoxy-4-nitrophenyl acetate

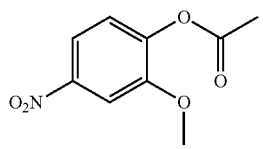

Following addition of acetyl chloride (0.50 mL, 7.10 mmol) to a solution of 4-nitroguaiacol (1.00 g, 5.91 mmol) and pyridine (0.52 mL, 7.10 mmol) in $CH_2Cl_2$ (10 mL) at RT, the mixture was stirred at RT for 30 min. The mixture was washed with 1M HCl (2×5 mL), dried ($Na_2SO_4$) and concentrated to provide the desired acetate (1.24 g, quant.) as a pale yellow solid: MS (electrospray, + ions) m/z 212 (M+H).

B. 4-Amino-2-methoxyphenyl acetate

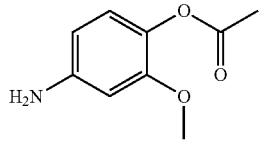

To a stirred solution of the 2-methoxy-4-nitrophenyl acetate prepared in Part A (99.2 mg, 0.47 mmol) in EtOAc (4.5 mL) was added palladium on carbon (33.0 mg, 5% dry basis, Degussa type: 50% water content). The suspension was hydrogenated (1 atm, balloon) for 3 h, filtered through CELITE® and the filter cake was rinsed with MeOH (5×10 mL). Evaporation of the combined filtrates gave the desired aniline (84.8 mg, quant.) as a brown oil: MS (electrospray, + ions) m/z 182 (M+H).

C. 4-(3-Amino-5-(4-chlorophenyl)thiophene-2-carboxamido)-2-methoxyphenyl acetate

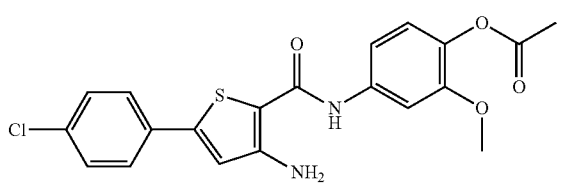

To a solution of 3-amino-5-(4-chlorophenyl)thiophene-2-carboxylic acid prepared in Example 1, Part A (104 mg, 0.41 mmol) in NMP (1.8 mL) were added O-(7-azabenzotriazol-1-yl)-N,N,N',N'-tetramethyluronium hexafluorophosphate (HATU) (195 mg, 0.51 mmol) and N,N-diisopropylethylamine (0.22 mL, 1.26 mmol). After the resulting solution was stirred at RT for 2.3 h, a solution of the aniline prepared in Part B of Example 2 (84.3 mg, 0.465 mmol) in 1,2-dichloroethane (0.8 mL+0.4 mL rinse) was added. After heating at 80° C. with stirring for 16 h, the reaction was cooled to RT before being diluted first with water (30 mL) and then sat'd NaHCO$_3$ (5.5 mL). Following extraction of the aqueous mixture (pH ~9) with EtOAc (3×30 mL), the combined organic extracts were washed with water (20 mL), dried (Na$_2$SO$_4$) and evaporated. Chromatography (SiO$_2$ 230-400 mesh, 9/1 CH$_2$Cl$_2$/Ether) of the crude provided the desired amide (118.2 mg, 69% yield) as a yellow solid: MS (electrospray, + ions) m/z 417 (M+H).

D. 4-(6-(4-Chlorophenyl)-4-oxothieno[3,2-d][1,2,3]triazin-3(4H)-yl)-2-methoxyphenyl acetate

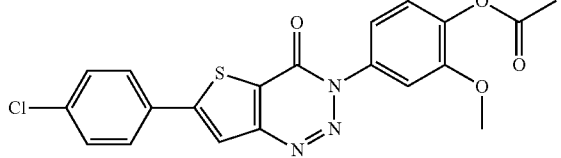

Following addition of NaNO$_2$ (21 mg, 0.30 mmol) to a stirred solution of the anilide of Part C of Example 2 (115 mg, 0.28 mmol) in AcOH (3.4 mL) and water (0.7 mL), stirring was continued at RT for 2 h. The reaction mixture was poured onto water (25 mL); whereupon, the pH of the aqueous mixture was adjusted to 8 by addition of 1M K$_2$CO$_3$. The resulting precipitate was collected by filtration, washed with water and dried to afford the title compound (111.5 mg, 94% yield) as a brown solid: MS (electrospray, + ions) m/z 428 (M+H).

E. 6-(4-Chlorophenyl)-3-(4-hydroxy-3-methoxyphenyl)thieno[3,2-d][1,2,3]triazin-4(3H)-one

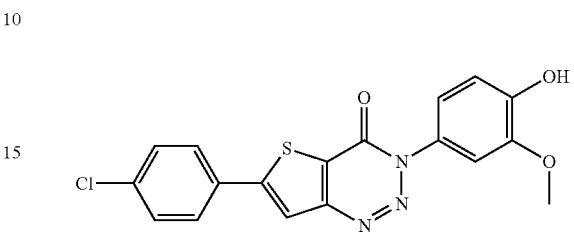

The triazinone of Part D of Example 2 (95.0 mg, 0.22 mmol) was treated with ~1M HCl/CH$_2$Cl$_2$, MeOH, MeOAc (prepared by addition of 0.8 mL of AcCl to 10 mL of 4/1 CH$_2$Cl$_2$/MeOH at 0° C. and stirring at RT for 20 min) for 3 h. After concentration of the resulting solution under vacuum, the residue was repeatedly dissolved and co-evaporated with CH$_2$Cl$_2$ (3×4 mL) to remove any remaining solvents. After drying the residue under vacuum overnight, the expected phenol (83.1 mg, 97% yield) was obtained as a brown solid: MS (electrospray, + ions) m/z 386 (M+H).

F. 6-(4-Chlorophenyl)-3-(3-methoxy-4-(2-oxopropoxy)phenyl)thieno[3,2-d][1,2,3]triazin-4(3H)-one

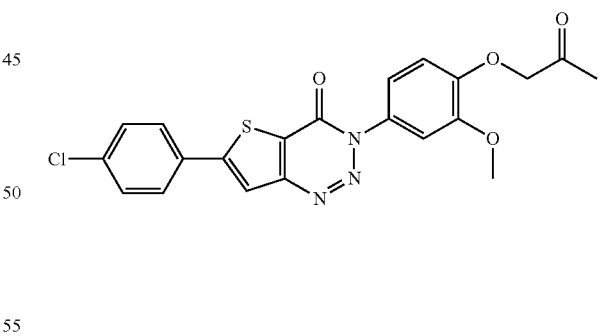

Chloroacetone (5.0 μL, 0.06 mmol) was added to a stirred suspension of the phenol prepared in Part E of Example 2 (15.4 mg, 0.04 mmol) and CsCO$_3$ (40.0 mg, 0.12 mmol) in MeCN (1.5 mL) at 80° C. After stirring at 80° C. for 2.3 h, the reaction was cooled to RT, diluted with CH$_2$Cl$_2$ (20 mL) and washed with water (8.0 mL). Following back-extraction of the aqueous wash with CH$_2$Cl$_2$ (2×10 mL), the combined organic layers were dried (Na$_2$SO$_4$) and evaporated. Chromatography (SiO$_2$ 230-400 mesh, 9/1CH$_2$Cl$_2$/Ether) of the crude

Example 3

6-(4-Chlorophenyl)-3-(4-(2-hydroxypropoxy)-3-methoxyphenyl)thieno[3,2-d][1,2,3]triazin-4(3H)-one

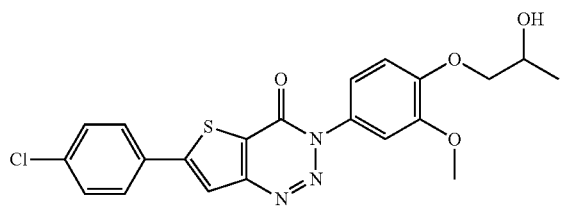

A stirred suspension of the methyl ketone prepared in Part F of Example 2 (15.6 mg, 0.035 mmol) in methanol (3.0 mL) and THF (1.5 mL) was stirred for 6 h at RT with NaBH$_4$ (1.8 mg, 0.05 mmol); whereupon, an additional amount of NaBH$_4$ (1.8 mg, 0.05 mmol) was added. After stirring an additional 2.6 h, the mixture was cooled to 0° C. and diluted with phosphate buffer (8 mL, 0.5M KH$_2$PO$_4$). The aqueous mixture was stirred at RT for 2 h after sufficient H$_3$PO$_4$ was added to lower the pH to 3 and then was extracted with CH$_2$Cl$_2$ (3×20 mL). The combined organic extracts were dried (Na$_2$SO$_4$) and concentrated. Chromatography (SiO$_2$ 230-400 mesh, 3/2 CH$_2$Cl$_2$/EtOAc) of the crude furnished the desired final product. (15.1 mg, 96% yield) as a yellow solid: MS (electrospray, + ions) m/z 444 (M+H); $^1$H NMR δ (CDCl$_3$) 7.75 (s, 1H), 7.69 (d, J=8.6 Hz, 2H), 7.51 (d, J=8.6, 2H), 7.21 (dd, J=8.4, 2.6 Hz, 1H), 7.18 (d, J=2.6 Hz 1H), 7.06 (d, J=8.4 Hz, 1H), 4.27 (m, 1H), 4.09 (dd, J 9.2, 2.7 Hz, 1H), 3.92 (s, 3H), 3.86 (t, J=9.2 Hz, 1H, overlapped), 1.29 (d, J=6.6 Hz, 3H).

Example 4

6-(4-Chlorophenyl)-3-(4-(2-hydroxyethoxy)-3-methoxyphenyl)thieno[3,2-d][1,2,3]triazin-4(3H)-one

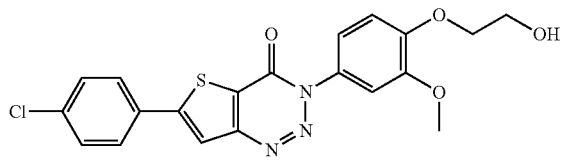

A stirred suspension of the phenol of Example 2, Part E (15.0 mg, 0.039 mmol), CsCO$_3$ (38.0 mg, 0.12 mmol) in MeCN (1.5 mL) and 2-(2-bromoethoxy)tetrahydro-2H-pyran (12 μL, 0.08 mmol) was heated at 80° C. for 12 h. After cooling to RT, the mixture was diluted with CH$_2$Cl$_2$ (20 mL) and washed with water (8.0 mL). After back-extraction of the aqueous wash with CH$_2$Cl$_2$ (2×10 mL), the combined organic layers were dried (Na$_2$SO$_4$) and evaporated under vacuum yield the crude pyranyl ether. Dissolution of the crude product in ~1M HCl in a mixture of CH$_2$Cl$_2$, MeOH and MeOTMS (prepared by stirring at RT for 50 min 3.2 mL of 5:3 CH$_2$Cl$_2$/MeOH to which 0.5 mL of TMSCl had been previously added at 0° C.) and stirring for 1 h removed the ether. After removal of the volatiles and co-evaporation with CH$_2$Cl$_2$ (3×4 mL), the residue was chromatographed (SiO$_2$ 230-400 mesh, 95/5 CH$_2$Cl$_2$/Ether) to afford the title compound (11.0 mg, 66% yield) as a yellow solid: MS (electrospray, + ions) m/z 430 (M+H);); $^1$H NMR 8 (CD$_2$Cl$_2$, 30° C.) 7.78 (s, 1H), 7.64 (d, J=8.4 Hz, 2H), 7.42 (d, J=8.4, 2H), 7.09 (m, 2H), 6.99 (d, J=7.9 Hz, 1H), 4.10 (t, J=4.5 Hz, 1H), 3.86 (t, J=4.5 Hz, 1H), 3.81 (s, 3H).

Example 5

6-(4-Chlorophenyl)-3-(4-(2-cyclopropyl-2-hydroxyethoxy)-3-methoxyphenyl)thieno[3,2-d][1,2,3]triazin-4(3H)-one

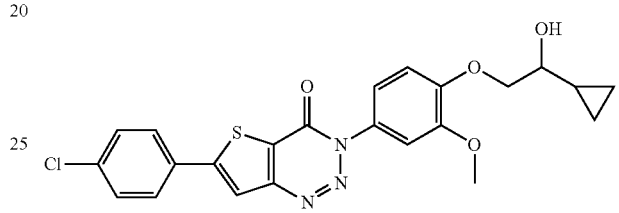

A. 6-(4-Chlorophenyl)-3-(4-(2-cyclopropyl-2-oxoethoxy)-3-methoxyphenyl)thieno[3,2-d][1,2,3]triazin-4(3H)-one

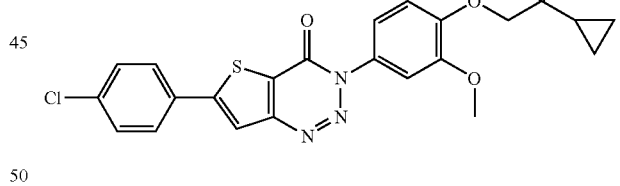

A stirred suspension of the phenol prepared in Example 2, Part E (14.4 mg, 0.037 mmol), CsCO$_3$ (37.0 mg, 0.11 mmol) and 2-cyclopropyl-2-oxoethyl 4-methylbenzenesulfonate (16.0 mg, 0.063 mmol) (*Tetrahedron Lett.*, 33:7647 (1992)) in MeCN (1.4 mL) was heated at 80° C. for 3.3 h. After cooling to RT, the mixture was diluted with CH$_2$Cl$_2$ (20 mL) and washed with water (8.0 mL). The aqueous layer was back-extracted with CH$_2$Cl$_2$ (2×10 mL); whereupon, the combined organic layers were dried (Na$_2$SO$_4$) and evaporated. Chromatography (SiO$_2$ 230-400 mesh, 95/5 CH$_2$Cl$_2$/Ether) of the crude afforded the title compound (15.5 mg, 89% yield) as a yellow solid: MS (electrospray, + ions) m/z 468 (M+H).

B. 6-(4-Chlorophenyl)-3-(4-(2-cyclopropyl-2-hy-droxyethoxy)-3-methoxyphenyl)thieno[3,2-d][1,2,3]triazin-4(3H)-one

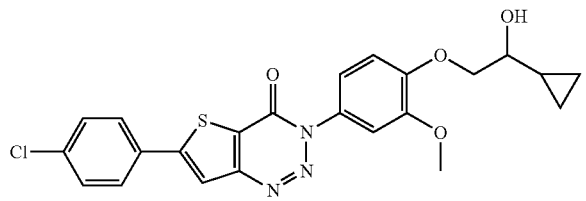

After addition of NaBH$_4$ (1.5 mg, 0.04 mmol) to a stirred suspension of the ketone prepared in Part A of Example 5 (14.4 mg, 0.031 mmol) in MeOH (3.0 mL) and THF (1.0 mL) at RT, the mixture was stirred at RT was for 3.7 h prior to adding additional NaBH$_4$ (1.5 mg, 0.04 mmol). The reaction was stirred for 10 h, cooled to 0° C. and quenched by addition of aq. phosphate buffer (8 mL of 0.5M KH$_2$PO$_4$ adjusted to pH 3 with H$_3$PO$_4$). The aqueous mixture was stirred at RT for 3 h before being extracted with CH$_2$Cl$_2$ (3×25 mL). The combined organic extracts were dried (Na$_2$SO$_4$) and concentrated. After drying under vacuum, the desired alcohol (14.2 mg, 98% yield) was isolated as a brownish solid: MS (electrospray, + ions) m/z 470 (M+H); $^1$H NMR (CD$_2$Cl$_2$, 25° C.) 7.79 (s, 1H), 7.64 (d, J=8.8 Hz, 2H), 7.42 (d, J=8.8, 2H), 7.08 (m, 2H), 7.00 (d, J=8.3 Hz, 1H), 4.15 (dd, J=9.9, 2.8 Hz, 1H), 3.77 (dd, J=9.9, 8.3 Hz, 1H), 3.80. (s, 3H), 3.27 (dt, J=2.8, 8.3 Hz, 1H), 0.91. (m, 1H), 0.49 (m, 2H), 0.35 (m, 1H), 0.26 (m, 1H).

Example 6

6-(4-Chlorophenyl)-3-(3-methoxy-44(4R,5R)-2,2,5-trimethyl-1,3-dioxolan-4-yl)methoxy)phenyl)thieno[3,2-d][1,2,3]triazin-4(3H)-one

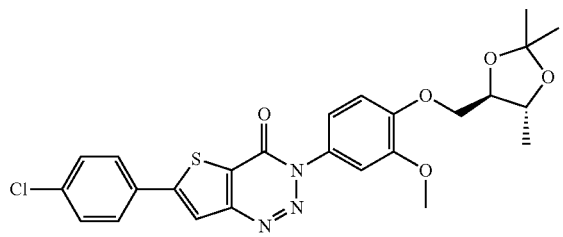

A. ((4R,5R)-2,2,5-trimethyl-1,3-dioxolan-4-yl)methanol

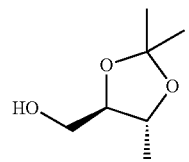

To a solution of commercial (4S,5R)-methyl 2,2,5-trimethyl-1,3-dioxolane-4-carboxylate (2.5 g, 14.4 mmol) in CH$_2$Cl$_2$ (50 ml) at 0° C. was added 1M LiAlH$_4$/THF (35.9 ml, 35.9 mmol). After stirring overnight at RT and cooling to 0° C., EtOAc (5.0 mL) was added. Stirring was continued at RT for 30 min prior to addition of water (50 mL); whereupon, the aqueous mixture was extracted with EtOAc (2×100 mL). The combined organic extracts were washed with sat'd NaCl, dried (Na$_2$SO$_4$), and concentrated. Chromatography (SiO$_2$ 230-400 mesh, Hex to 85/15 Hex/EtOAc) of the crude product afforded the expected alcohol (1.18 g, 56% yield) as a clear liquid: $^1$H NMR δ (CDCl$_3$) 4.02 (m, 1H), 3.81 (dd, J=12.1, 2.8 Hz, 1H), 3.65 (m, 1H), 3.60 (dd, J=12.1, 4.4 Hz, 1H), 1.43 (s, 1H), 1.40 (s, 3H), 1.29 (d, J=6.1 Hz, 3H).

B. ((4R,5R)-2,2,5-Trimethyl-1,3-dioxolan-4-yl)methyl 4-methylbenzenesulfonate

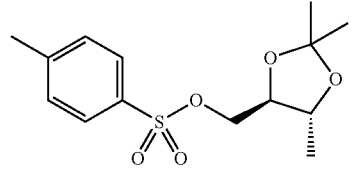

A solution of the alcohol prepared in Part A of Example 6 (434 mg, 2.97 mmol), Et$_3$N (0.83 ml, 5.94 mmol), DMAP (50 mg, 2.97 mmol) and tosyl chloride (623 mg, 327 mmol) in CH$_2$Cl$_2$ (100 ml) was stirred at RT for 30 min. The reaction mixture was concentrated and the resulting yellow residue was chromatographed (SiO$_2$ 230-400 mesh, gradient elution employing hexane to 85:15 hexane/EtOAc) to elute the expected tosylate (804 mg, 89% yield) as a clear liquid: MS (electrospray, + ions) m/z 301 (M+H).

C. 6-(4-Chlorophenyl)-3-(3-methoxy-4-(((4R,5R)-2,2,5-trimethyl-1,3-dioxolan-4-yl)methoxy)phenyl)thieno[3,2-d][1,2,3]triazin-4(3H)-one

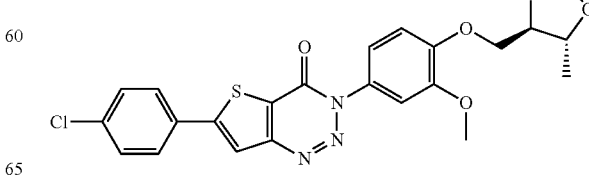

Following addition of the tosylate prepared in Part B of Example 6 (20.0 mg, 0.067 mmol) to a stirred suspension of the phenol prepared in Example 2, Part E (13.5 mg, 0.035 mmol) and CsCO₃ (70.0 mg, 0.22 mmol) in MeCN (1.4 ml) at 80° C., the mixture was stirred at 80° C. for 48 h. After cooling to RT, the mixture was diluted with CH₂Cl₂ (20 mL) and washed with water (8.0 mL). The aqueous wash was back-extracted with CH₂Cl₂ (2×10 mL). The combined organic layers were dried (Na₂SO₄) and evaporated. Chromatography (SiO₂ 230-400 mesh, 9:1 CH₂Cl₂/Ether) of the crude product eluted the acetonide (11.5 mg, 64% yield) as an orange solid: MS (electrospray, + ions) m/z 514 (M+H).

Example 7

6-(4-Chlorophenyl)-3-(4-((2R,3R)-2,3-dihydroxybutoxy)-3-methoxyphenyl)thieno[3,2-d][1,2,3]triazin-4(3H)-one

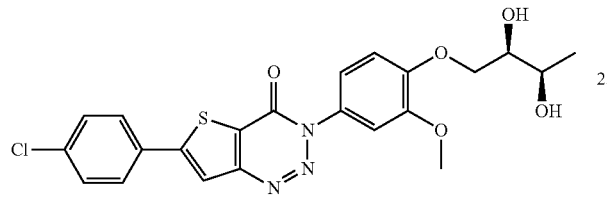

The acetonide prepared in Part C of Example 6 (10.4 mg, 0.02 mmol) was stirred for 1 hr at RT in a ~1M HCl mixture of CH₂Cl₂, MeOH and MeOTMS (prepared by stirring at RT for 50 min 3.2 mL of 5:3 CH₂Cl₂/MeOH to which 0.5 mL of TMSCl had been previously added at 0° C.). After evaporation of the volatiles, any residual volatile components were removed upon co-evaporation with CH₂Cl₂/MeOH (3×4 mL). Chromatography of the non-volatile residue (SiO₂ 230-400 mesh, 95/5 CH₂Cl₂/MeOH) eluted the desired dial (8.1 mg, 84% yield) as a brownish solid: MS (electrospray, + ions) m/z 474 (M+H); ¹H NMR δ (CD₂Cl₂+CD₃OD drops, 30° C.) 7.91 (s, 1H), 7.75 (d, J=8.4 Hz, 2H), 7.52 (d, J=8.4, 2H), 7.19 (m, 2H), 7.09 (d, J=8.8 Hz, 1H), 4.19 (dd, J=9.7, 3.5 Hz, 1H), 4.27 (dd, J=9.7, 6.6 Hz, 1H), 3.94. (m, 1H, overlapped), 3.92 (s, 3H), 3.80. (m, 1H), 1.27 (d, J=6.2 Hz, 3H).

Example 8

6-(4-Chlorophenyl)-3-(3-methoxy-4-(3,3,3-trifluoro-2-hydroxypropoxy)phenyl)thieno[3,2-d][1,2,3]triazin-4(3H)-one

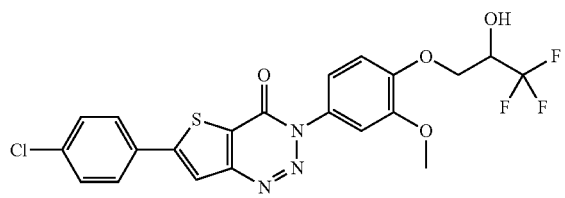

A stirred suspension of the phenol prepared in Example 2, Part E (9.0 mg, 0.023 mmol), 2-(trifluoromethyl)oxirane (25.0 pt, 0.29 mmol) and CsCO₃ (76.0 mg, 0.23 mmol) in MeCN (1.4 mL) was heated at 82° C. in a sealed flask for 18 h. After cooling to RT, the mixture was diluted with CH₂Cl₂ (30 mL) and washed with water (10.0 mL); whereupon, the aqueous wash was back-extracted with CH₂Cl₂ (2×10 mL). The combined organic layers were dried (Na₂SO₄) and evaporated. Chromatography (SiO₂ 230-400 mesh, 9/1 CH₂Cl₂/Ether) of the crude product eluted the title compound (6.6 mg, 57% yield) as a yellowish solid: MS (electrospray, + ions) m/z 498 (M+H); ¹H NMR δ (CD₂Cl₂, 30° C.) 7.88 (s, 1H), 7.73 (d, J=8.8 Hz, 2H), 7.51 (d, J=8.8, 2H), 7.21 (m, 2H), 7.13 (m, 1H), 4.40 (m, 1H), 4.36 (dd, J=10.1, 3.5 Hz, 1H), 4.27 (dd, J=10.1, 6.6 Hz, 1H), 3.92 (s, 3H), 3.39 (d, J=5.7 Hz, 1H, —OH).

Example 9

2-(4-Chlorophenyl)-6-(4-(2-hydroxy-2-methylpropoxy)-3-methoxyphenyl)-thieno[2,3-d]pyridazin-7(6H)-one

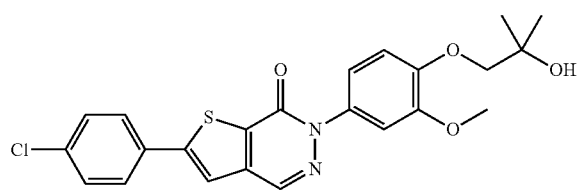

A.
1-(4-Bromo-2-methoxyphenoxy)-2-methylpropan-2-ol

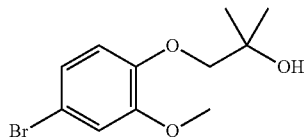

A mixture of 4-bromo-2-methoxyphenol (5 g, 24.63 mmol), NaH₂PO₄ monohydrate (3.23 g, 23.40 mmol) and 2,2-dimethyloxirane (3.02 g, 41.9 mmol) in MeCN (90 ml) and H₂O (10.00 ml) was stirred at 150° C. in a steel bomb for 4 hours. After cooling to RT, the mixture was diluted with a solution of saturated NaHCO₃ (80 ml) and extracted with EtOAc (80 ml). The EtOAc extracts were dried over Na₂SO₄ and concentrated. The crude product was purified by ISCO chromatography on a silica gel column (120 g) employing a 10 min gradient ranging from hexane to 30% EtOAc/hexane to elute 1-(4-bromo-2-methoxyphenoxy)-2-methylpropan-2-ol (6.25 g, 22.72 mmol, 92% yield) as clear oil. LC MS at t=2.24 min. (m Na=297) PHENOMENEX® S5 C18 4.6×30 mm column/water-MeOH-TFA 90:10:0.1 to 10:90:0.1 gradient over 2 min at 5 mL/min with 1 min hold at the end of the gradient. $^1$H NMR (400 MHz, CDCl$_3$) δ ppm 1.33 (s, 6H), 3.79 (s, 2H), 3.84 (s, 3H), 6.77 (d, J=8.31 Hz, 2H), 7.01 (s, 1H), 7.26 (s, 1 H).

B. 5-(4-Chlorophenyl)thiophene-2-carboxylic acid

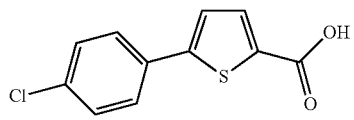

A mixture of ethyl 5-bromothiophene-2-carboxylate (1.0 g, 4.25 mmol), 4-chlorophenylboronic acid (0.998 g, 6.38 mmol), 2.0 M aq NaHCO$_3$ (6.38 ml, 12.76 mmol) and tetrakis(triphenylphosphine)palladium(0) (0.492 g, 0.425 mmol) in DMF (40 ml) under nitrogen was stirred at 100° C. under nitrogen in a sealed tube for 18 hours as described in WO 2007/011284. The reaction was then cooled to RT, diluted with saturated aq NaHCO$_3$ (40 ml) and extracted with EtOAc (40 ml). The EtOAc extracts were dried over Na$_2$SO$_4$ and concentrated. The crude product was purified by ISCO chromatography on a silica gel column (120 g) employing a 10 min gradient ranging from hexane to 30% EtOAc to elute ethyl 5-(4-chlorophenyl)thiophene-2-carboxylate (1.05 g, 3.94 mmol, 93% yield) as a white solid. LC MS at t=2.70 min. (m+H=267) PHENOMENEX® 55 C18 4.6×30 mm column/water-MeOH-TFA 90:10:0.1 to 10:90:0.1 gradient over 2 min at 5 mL/min with 1 min hold at the end of the gradient. $^1$H NMR (400 MHz, CD$_3$OD) δ ppm 1.39 (t, J=7.18 Hz, 3H), 4.37 (q, J=7.22 Hz, 2H), 7.43-7.51 (m, 3H), 7.71 (d, J=8.56 Hz, 2H), 7.78 (d, J=4.03 Hz, 1H).

A mixture of ethyl 5-(4-chlorophenyl)thiophene-2-carboxylate (1.05 g, 3.94 mmol), methanol (40 ml) and 1.0 M aq NaOH (15.75 ml, 15.75 mmol) was stirred at reflux for 6 hours. Upon cooling to RT, the reaction was acidified to pH 3 with conc. HCl and extracted with EtOAc (60 ml). The EtOAc layer was dried over Na$_2$SO$_4$ and concentrated to yield 5-(4-chlorophenyl)thiophene-2-carboxylic acid (902 mg, 3.78 mmol, 96% yield) as an off-white solid. LC MS at t=2.44 min. (m+H=240) PHENOMENEX® S5 C18 4.6×30 mm column/water-MeOH-TFA 90:10:0.1 to 10:90:0.1 gradient over 2 min at 5 mL/min with 1 min hold at the end of the gradient. $^1$H NMR (400 MHz, DMSO) δ ppm 7.36-7.97 (m, 6H), 13.19 (s, 1H).

C. (4-Chlorophenyl)thieno[3,2-d]pyridazin-7(6H)-one

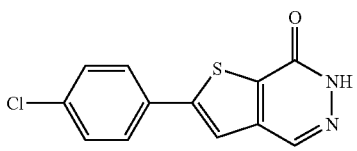

To a solution of 5-(4-chlorophenyl)thiophene-2-carboxylic acid (890 mg, 3.73 mmol) in anhydrous THF (40 ml) under N$_2$ at −78° C. was added a solution of 1.6 M n-butyllithium in hexane (5.83 ml, 9.32 mmol). The reaction was allowed to warmed to 0° C. over 3 hours whereupon the solution was cooled to −78° C. prior to addition of DMF (2.89 ml, 37.3 mmol). After stirring the mixture at −50° C. for 2 hours, the reaction was quenched with aqueous 1 N HCl (20 ml) prior to extraction with EtOAc (40 ml). The EtOAc extracts were dried over Na$_2$SO$_4$ and concentrated to give light brown solid. Following dissolution of the brown solid in MeOH (20 ml), hydrazine (0.351 ml, 11.19 mmol) was added, followed by conc. HCl (1 ml). The mixture was stirred at reflux for 2 days; whereupon after cooling to RT, the mixture was diluted with a solution of saturated NaHCO$_3$ (15 ml). The resulting precipitate was collected by filtration, washed with water and EtOAc to yield after drying 2-(4-chlorophenyl)thieno[3,2-d]pyridazin-7(6H)-one (860 mg, 3.28 mmol, 87% yield) as brown solid. LC MS at t=2.25 min. (m+H=263) PHENOMENEX® S5 C18 4.6×30 mm column/water-MeOH-TFA 90:10:0.1 to 10:90:0.1 gradient over 2 min at 5 mL/min with 1 min hold at the end of the gradient. $^1$H NMR (400 MHz, DMSO) δ ppm 7.59 (d, J=8.56 Hz, 2H), 7.88 (d, J=8.56 Hz, 2H), 7.99 (s, 1H), 8.40 (s, 1H), 12.99 (s, 1H)

D. 2-(4-Chlorophenyl)-6-(4-(2-hydroxy-2-methylpropoxy)-3-methoxyphenyl)-thieno[2,3-d]pyridazin-7(6H)-one

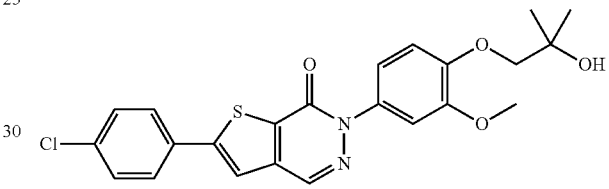

A mixture of 1-(4-bromo-2-methoxyphenoxy)-2-methylpropan-2-ol (157 mg, 0.571 mmol), 2-(4-chlorophenyl)thieno[2,3-d]pyridazin-7(6H)-one (150 mg, 0.571 mmol), (1R,2R)—N1,N2-dimethylcyclohexane-1,2-diamine (24.36 mg, 0.171 mmol), K$_3$PO$_4$ (0.142 ml, 1.713 mmol) and cupric oxide (24.51 mg, 0.171 mmol) in dioxane (4 ml) was stirred at 130° C. under N$_2$ in a sealed tube for 24 hours. Since LC-MS analysis revealed no product, another portion of cupric oxide (24.51 mg, 0.171 mmol) was added to the mixture which was then was stirred at 130° C. under N$_2$ in a sealed tube for another 24 hours. Since LC-MS analysis indicated only 25% conversion to product, another equivalent of copper (I) oxide and dimethylcyclohexane-1,2-diamine was added. The mixture was stirred at 150° C. under N$_2$ in a seal tube for 8 hours. After cooling to RT, LC-MS analysis showed the conversion was 45% to product. The mixture was diluted with CH$_2$Cl$_2$ (40 ml) prior to removal of the inorganic solid by filtration. The CH$_2$Cl$_2$ filtrate was washed with a solution of saturated NaHCO$_3$ (3×40 ml), dried over Na$_2$SO$_4$ and concentrated. The crude product was purified by ISCO chromatography on two silica gel column (2×4.0 g) employing a 10 min gradient ranging from hexane to 100% ethyl acetate to elute partially pure product. After titration with MeOH, 2-(4-chlorophenyl)-6-(4-(2-hydroxy-2-methylpropoxy)-3-methoxyphenyl)thieno[2,3-d]pyridazin-7(6H)-one (101 mg, 0.221 mmol, 38.7% yield) was obtained as light brown solid. LC MS at t=2.52 min. (m+H=457) PHENOMENEX® S5 C18 4.6X30 mm column/water-MeOH-TFA 90:10:0.1 to 10:90:0.1 gradient over 2 min at 5 mL/min with 1 min hold at the end of the gradient. $^1$H NMR (400 MHz, CDCl$_3$) δ ppm 1.36 (s, 6H), 3.89 (d, J=3.78 Hz, 5H), 7.00 (d, J=8.56 Hz, 1H), 7.17-7.24 (m, 2H), 7.42-7.54 (m, 3H), 7.66 (d, J=8.31 Hz, 2H), 8.31 (s, 1H).

Prodrugs were prepared of selected secondary and tertiary alcohols to improve solubility and exposure. Preparation of the glycine ester of the tertiary alcohols is exemplified in Examples 10 and 11.

Example 10

1-(4-(6-(4-Chlorophenyl)-4-oxothieno[3,2-d][1,2,3]triazin-3(4H)-yl)-2-methoxyphenoxy)-2-methylpropan-2-yl 2-aminoacetate

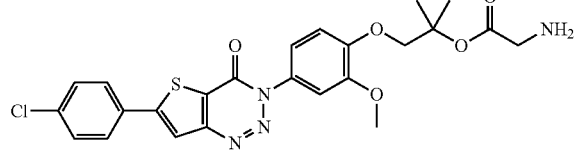

A. 1-(4-(6-(4-Chlorophenyl)-4-oxothieno[3,2-d][1,2,3]triazin-3(4H)-yl)-2-methoxyphenoxy)-2-methylpropan-2-yl 2-(tert-butoxycarbonylamino)acetate

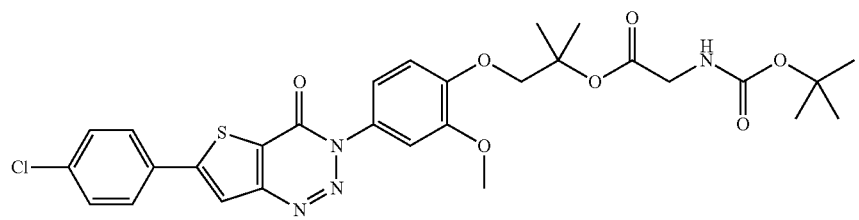

To a stirred suspension of the alcohol prepared in Part D of Example 1 (230 mg, 0.50 mmol), 4-pyrrolidinopyridine (114 mg, 0.75 mmol) and BOC-Gly-OH (264 mg, 1.51 mmol) in $CH_2Cl_2$ (9.0 mL) at 42° C. was added N,N'-diisopropylcarbodiimide (0.23 mL, 1.51 mmol) over 1 h. After stirring at 42° C. for 2.5 h, more BOC-Gly-OH (264 mg, 1.51 mmol) was added followed by additional N,N'-diisopropylcarbodiimide (0.23 mL, 1.51 mmol) which was slowly added over 1 h. Stirring was continued at 42° C. for 1 h; whereupon, the mixture was allowed to cool to RT prior to addition of hydrazine monohydrate (150 μL, 3.09 mmol). After stirring for an additional 1 h, the reaction mixture was cooled to 0° C. and filtered. The filtrates were sequentially washed with cold 1M HCl (3×20 mL) and cold 2% $NaHCO_3$ (3×20 mL) prior to drying ($Na_2SO_4$) and concentrating under vacuum. Chromatography ($SiO_2$ 230-400 mesh, 9:1 $CH_2Cl_2$/Ether) of the residue afforded the desired ester (296 mg, 96% yield) as a yellow solid: MS (electrospray, + ions) m/z 615 (M+H).

B. 1-(4-(6-(4-Chlorophenyl)-4-oxothieno[3,2-d][1,2,3]triazin-3(4H)-yl)-2-methoxyphenoxy)-2-methylpropan-2-yl 2-aminoacetate

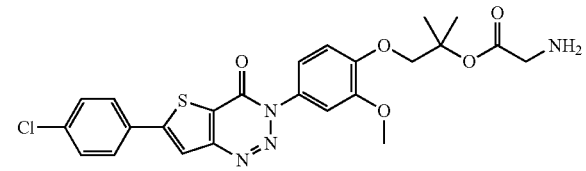

The BOC'd glycinate ester described in Part B (295 mg, 0.48 mmol) was treated with 1:2 TFA/$CH_2Cl_2$ (13.5 mL) at RT for 20 min. After removal of the volatiles under vacuum, the residual TFA was removed by co-evaporation with $CH_2Cl_2$ (3×8 mL) and drying under vacuum for 20 min. Following dissolution in $CH_2Cl_2$ (70 mL), the solution was washed with cold 5% $NaHCO_3$ (3×30 mL) dried ($Na_2SO_4$) and concentrated to yield the desired free amine (228 mg, 92% yield) as a reddish solid: MS (electrospray, + ions) m/z 515 (M+H).). $^1$H NMR δ ($CDCl_3$) 7.85 (s, 1H), 7.69 (d, J=8.8 Hz, 2H), 7.49 (d, J=8.8, 2H), 7.18 (m, 2H), 7.04 (d, J=8.4 Hz, 1H), 4.25 (s, 2H), 3.90 (s, 3H), 3.34 (s, 2H) 1.63 (s, 6H).

Example 11

A. 1-(4-(2-(4-Chlorophenyl)-7-oxothieno[2,3-d]pyridazin-6(7H)-yl)-2-methoxyphenoxy)-2-methylpropan-2-yl 2-(tent-butoxycarbonylamino)acetate

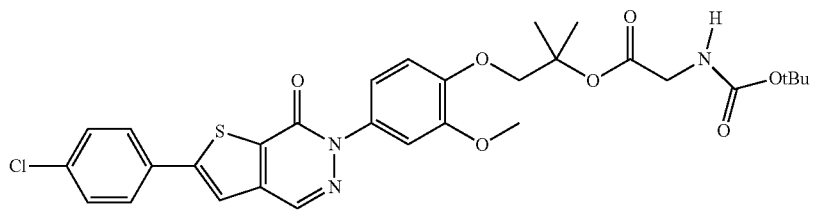

To a solution of 2-(4-chlorophenyl)-6-(4-(2-hydroxy-2-methylpropoxy)-3-methoxyphenyl)thieno[2,3-d]pyridazin-7(6H)-one (100 mg, 0.219 mmol) that was prepared in Example 9,4-(pyrrolidin-1-yl)pyridine (32.4 mg, 0.219 mmol) and boc-glycine (192 mg, 1.094 mmol) in CH$_2$Cl$_2$ (10 ml) was added N,N'-diisopropylcarbodiimide (0.170 ml, 1.094 mmol). The mixture was stirred at reflux for 1 hours and then at RT for 18 hours. LC-MS analysis revealed desired product as well as the imide resulting from condensation with a second Boc-glycine. The later product was cleaved to regenerate desired product by addition of hydrazine (0.343 ml, 10.94 mmol) was added and the stirring at RT for 30 min. The reaction was diluted with a solution of saturated NaHCO$_3$ (15 ml) and extracted with CH$_2$Cl$_2$ (20 ml). The CH$_2$Cl$_2$ extracts were dried over Na$_2$SO$_4$ and concentrated. The crude product was purified by ISCO chromatography on two silica gel column (2×12 g) employing a 10 min gradient ranging from hexane to 100% ethyl acetate to elute 1-(4-(2-(4-chlorophenyl)-7-oxothieno[2,3-d]pyridazin-6(7H)-yl)-2-methoxyphenoxy)-2-methylpropan-2-yl 2-(tert-butoxycarbonylamino)acetate (130 mg, 0.212 mmol, 97% yield) as light brown solid.

B. 1-(4-(2-(4-Chlorophenyl)-7-oxothieno[2,3-d]pyridazin-6(7H)-yl)-2-methoxyphenoxy)-2-methylpropan-2-yl2-aminoacetate

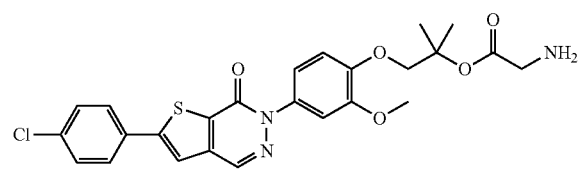

To a solution of 1-(4-(2-(4-chlorophenyl)-7-oxothieno[2,3-d]pyridazin-6(7H)-yl)-2-methoxyphenoxy)-2-methylpropan-2-yl 2-(tert-butoxycarbonylamino)acetate (130 mg, 0.212 mmol) in CH$_2$Cl$_2$ (10 ml) was added trifluoroacetic acid (3 ml, 38.9 mmol). The reaction was stirred at RT for 30 min, concentrated and redissolved in CH$_2$Cl$_2$ (15 ml). The CH$_2$Cl$_2$ solution was washed with a saturated NaHCO$_3$ (15 ml), dried over Na$_2$SO$_4$ and concentrated. The crude product was purified by ISCO chromatography on silica gel column (12 g) employing a 10 min gradient ranging from hexane to 100% EtOAc to elute less polar impurities; desired product was eluted with 1% NH$_4$OH:9% MeOH:90% CH$_2$Cl$_2$. The pure product was isolated as the hydrochloride salt following dissolution in CH$_2$Cl$_2$ (15 ml) and addition of a solution of aqueous 1.0M HCl in MeOH (3 ml) at −30° C. to give HCl salt. After filtration and drying, the hydrochloride of 1-(4-(2-(4-chlorophenyl)-7-oxothieno[2,3-d]pyridazin-6(7H)-yl)-2-methoxyphenoxy)-2-methylpropan-2-yl 2-aminoacetate (82.49 mg, 0.160 mmol, 73.3% yield) was obtained as off-white solid. LC MS at t=2.28 min. (m+H=514) PHENOMENEX® S5 C18 4.6×30 mm column/water-MeOH-TFA 90:10:0.1 to 10:90:0.1 gradient over 2 min at 5 mL/min with 1 min hold at the end of the gradient. $^1$H NMR (400 MHz, DMSO) δ ppm 1.60 (s, 6H), 3.76 (s, 2H), 3.81 (s, 3H), 4.24 (s, 2H), 7.13 (s, 2H), 7.25 (s, 1H), 7.63 (d, J=8.56 Hz, 2H), 7.93 (d, J=8.56 Hz, 2H), 8.06 (s, 1H), 8.57 (s, 1H).

Biological Evaluation

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl2, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC UNIFILTER® plates pre-coated with 0.075 ml binding buffer containing 1% BSA, and washed 3 times with 0.4 ml of Phospho-buffered Saline (pH 7.4) containing 0.01% TX-100. Filters were dried, 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

| Example | hMCHR1 K$_i$ (nM) |
| --- | --- |
| 1 | 3 |
| 2 | 5 |
| 3 | 7 |
| 4 | 5 |
| 5 | 10 |
| 6 | 19 |
| 7 | 5 |
| 8 | 8 |
| 9 | 4 |

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound having the following Formula I, or a pharmaceutically acceptable salt thereof:

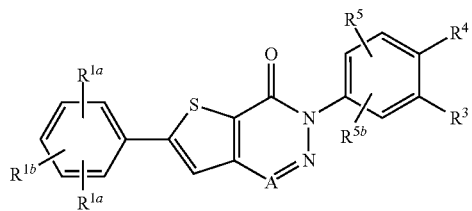

I wherein,

A is $CR^2$;

$R^1$, $R^{1b}$ and $R^{1a}$ are the same or different and are each independently selected from the group consisting of H, halo, lower alkyl, cycloalkyl, $CF_3$, alkoxy, and thioalkoxy;

$R^2$ is H or lower alkyl;

$R^3$ is H, halo, lower alkyl, cycloalkyl, $CF_3$, lower alkoxy, thioalkoxy, or CN;

$R^4$ is —OH or -G-D-$Z_n$;

$R^5$ and $R^{5b}$ are the same or different and are each independently selected from the group consisting of H, halo, and lower alkyl;

n is 1 to 3;

G is O or S;

D is selected from the group consisting of lower alkyl, cycloalkylalkyl, cycloalkyl and

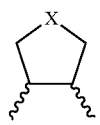

wherein X is —O—, —S—, —SO— or —$SO_2$—;

Z is independently hydrogen, hydroxyl, polyhaloalkyl, lower alkyl, lower alkoxy, cycloalkyl, cycloalkoxy, $OCONR^6R^7$, CN, $CONR^8R^9$, $SOR^{10}$, $SO_2R^{11}$, $NR^{12}COR^{13}$, $NR^{14}CO_2R^{15}$, $COR^{16}$, a 5- to 6-membered heteroaryl, or a 4- to 6-membered heterocycloalkyl containing no more that two heteroatoms wherein the heteroatoms are independently —O—, —S—, —SO— or —$SO_2$—;

$R^6$, $R^7$, $R^8$, $R^9$, $R^{12}$ and $R^{14}$ are the same or different and are each independently selected from the group consisting of H, lower alkyl and cycloalkyl or $R^6$ and $R^7$ and/or $R^8$ and $R^9$ together with the atoms to which they are attached may form a 4- to 7-membered ring; and $R^{10}$, $R^{11}$ $R^{13}$, $R^{15}$ and $R^{16}$ are the same or different and are each independently selected from the group consisting of lower alkyl, and cycloalkyl.

2. The compound of claim 1 wherein $R^4$ is -G-D-$Z_n$.

3. The compound as defined in claim 2 wherein D is selected from the group consisting of a direct bond, lower alkyl, cycloalkylalkyl, cycloalkyl and

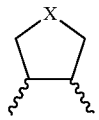

wherein X is —O—, —S—, —SO— or —$SO_2$— and is 1,3-dioxalane, 1,3-dithiolane, tetrahydrofuran, tetrahydrothiophene, tetrahydrothiophene-1-oxide, sulfolane, 1,4-oxathiane, 1,4-oxathiane-1-oxide, 1,4-oxathiane-1,1-dioxide, 1,3-dithiane, 1,4-dithiane, 1,3-dioxane, 1,4-dioxane, 1,3-oxathiolane, 1,3-oxathiolane-1-oxide, or 1,3-oxathiolane-1,1-dioxide.

4. The compound as defined in claim 3 wherein D is lower alkyl.

5. The compound of claim 1 wherein Z is $COR^{16}$, —OH, dioxylanyl, or $CF_3$.

6. The compound of claim 1 wherein $R^3$ is alkoxy and $R^1$ is halogen.

7. The compound of claim 1 wherein $R^3$ is methoxy, $R^1$ is Cl and $R^{1a}$, $R^{1b}$, $R^5$ and $R^{5b}$ are H.

8. The compound of claim 1 wherein $R^4$ is -G-D-$Z_n$; D is lower alkyl; Z is —OH, dioxylanyl, or $CF_3$; $R^3$ is methoxy; $R^1$ is Cl; and $R^{1a}$, $R^{1b}$, $R^5$, and $R^{5b}$ are H.

9. The compound as defined in claim 1 having the structure

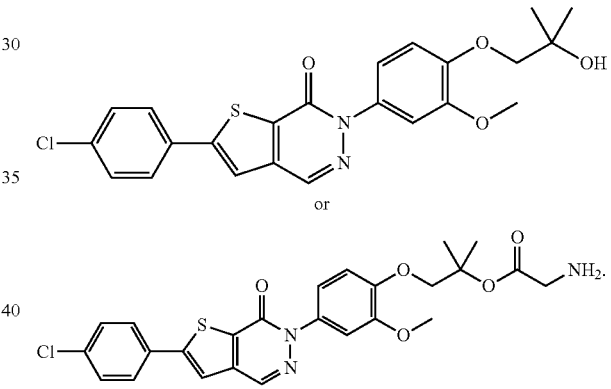

10. A pharmaceutical composition, comprising one or more compounds according to claim 1 or a pharmaceutically acceptable salt thereof and at least one pharmaceutically acceptable diluent or carrier.

11. The pharmaceutical composition according to claim 10, further comprising at least one additional therapeutic agent.

12. A pharmaceutical combination, comprising one or more compounds according to claim 1 or a pharmaceutically acceptable salt thereof and at least one additional therapeutic agent selected from the group consisting of anti-obesity agents; anti-diabetic agents, appetite suppressants; cholesterol/lipid-lowering agents, and HDL-raising agents.

13. The pharmaceutical combination according to claim 12 wherein said additional therapeutic agent is an anti-diabetic agent.

14. The pharmaceutical combination of claim 13, wherein said anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors, PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PTP-1B inhibitors.

15. The pharmaceutical combination of claim 14 wherein said additional therapeutic agent is an antiobesity agent selected from group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, Pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor antagonists.

16. A method for treating obesity in a patient in need of such treatment, comprising administering a therapeutically effective amount of one or more compounds according to claim 1 or a pharmaceutically acceptable salt thereof alone or in combination with one or more antiobesity agents.

17. The method of claim 16 wherein said antiobesity agent is selected from the group consisting of melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, Pre-proglucagon-derived peptides; NPY1 or NPY5 antagonists; NPY2 and NPY4 modulators; orticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF, BDNF, DGAT inhibitors, leptin, leptin receptor modulators, and cannabinoid-1 receptor antagonists.

18. A method for treating diabetes in a patient in need of such treatment, comprising administering a therapeutically effective amount of one or more compounds according to claim 1 or a pharmaceutically acceptable salt thereof alone or in combination with one or more additional anti-diabetic agents.

19. The method according to claim 18 wherein said additional anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, insulin, glucagon-like peptide-1 (GLP-1), GLP-1 agonists, and PIP-1B inhibitors.

20. A method for treating depression or anxiety in a patient, comprising administering a therapeutically effective amount of one or more compounds according to claim 1 or a pharmaceutically acceptable salt thereof.

* * * * *

UNITED STATES PATENT AND TRADEMARK OFFICE
CERTIFICATE OF CORRECTION

PATENT NO. : 7,973,159 B2
APPLICATION NO. : 12/907451
DATED : July 5, 2011
INVENTOR(S) : William N. Washburn, Saleem Ahmad and Andres S. Hernandez Page 1 of 1

It is certified that error appears in the above-identified patent and that said Letters Patent is hereby corrected as shown below:

On the Title Page, Item (57)
Last Line, "Formula I." should read -- Formula I --

Column 41
Line 10-20

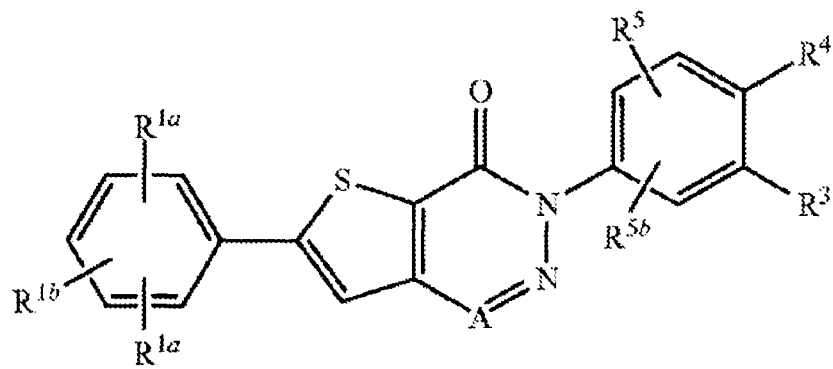

Should read --

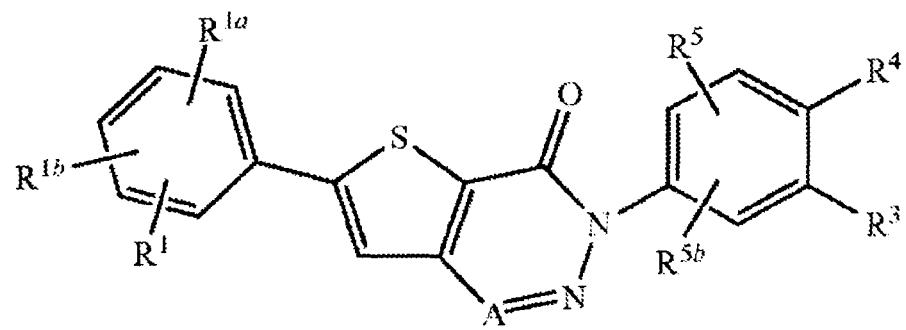

Signed and Sealed this
Fifteenth Day of November, 2011

David J. Kappos
*Director of the United States Patent and Trademark Office*